United States Patent [19]

Phillipps et al.

[11] Patent Number: 4,650,800

[45] Date of Patent: Mar. 17, 1987

[54] SUBSTITUTED PYRIMIDIN-2-ONES, THE SALTS THEREOF, PHARMACEUTICAL COMPOSITIONS CONTAINING THEM AND A METHOD THEREFOR

[75] Inventors: Gordon H. Phillipps, Wembley; Christopher Williamson, Cobham; Ian P. Steeples, Ruislip; Brian M. Bain, Chalfont St. Peter; Raymond A. Borella, Haringey, all of United Kingdom

[73] Assignee: Glaxo Group Limited

[21] Appl. No.: 496,093

[22] Filed: May 19, 1983

Related U.S. Application Data

[63] Continuation of Ser. No. 283,646, Jul. 15, 1981, abandoned.

[30] Foreign Application Priority Data

Jul. 15, 1980 [GB] United Kingdom ............. 8023083

[51] Int. Cl.[4] .................. A61K 31/505; C07D 403/06; C07D 405/06
[52] U.S. Cl. .................................. 514/259; 544/315; 544/316; 544/318; 548/540; 549/73
[58] Field of Search ............... 544/316, 318; 424/251; 514/259

[56] References Cited

PUBLICATIONS

Phillipps et al., "Chemical Abstracts", vol. 96, 1982, Cols. 181304c and 181305d.

Primary Examiner—Glennon H. Hollrah
Assistant Examiner—James H. Turnipseed
Attorney, Agent, or Firm—Bacon and Thomas

[57] ABSTRACT

Compounds of the general formula:

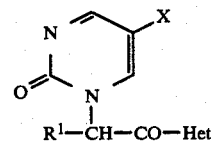

wherein X represents a halogen atom or a trifluoromethyl group; $R^1$ represents a hydrogen atom or a lower alkyl group and Het represents an optionally substituted C-attached 5–7 membered aromatic heterocyclic ring which ring contains one or more heteroatoms selected from O, N and S and optionally carries a fused ring and where an acidic or basic group is present, the salts thereof have been found to possess excellent metaphase arresting ability and are of use in combating abnormal cell proliferation. Thus a knowledge of the cell division cycles of the normal and abnormal cells enables a cytotoxic drug to be administered while the abnormal cells are in a phase susceptible to attack and while the normal cells are in a non-susceptible phase.

The compounds of the invention are prepared by alkylation, deprotection of a protected keto group, oxidation or electrophilic halogenation.

11 Claims, No Drawings

SUBSTITUTED PYRIMIDIN-2-ONES, THE SALTS THEREOF, PHARMACEUTICAL COMPOSITIONS CONTAINING THEM AND A METHOD THEREFOR

This application is a continuation of application Ser. No. 283,646, filed July 15, 1981, now abandoned.

The present invention relates to substituted pyrimidin-2-ones, the salts thereof, processes for their preparation, pharmaceutical compositions containing them and a method therefor.

Abnormal cell proliferation is present in a number of diseases such as cancers, leukaemias, cutaneous cellular proliferation, e.g. contact dematitis or psoriasis, or autoimmune diseases where proliferation of lymphocytes leads to an undesirable immune response against some of the normal tissues of the body.

A number of drugs are known which combat abnormal cell proliferation by destroying the cells in one of the phases of cell-division in which they are particularly susceptible to such attack. In general, the cell-division cycle of both normal and abnormal cells includes a succession of phases, usually termed the G1, S, G2 and M phases, the last-mentioned being mitosis which in itself includes four well defined phases, prophase, metaphase, anaphase and telophase, related to the rearrangement of chromasomal material in the cell. In general, DNA synthesis takes place in the S phase, while protein synthesis takes place in the G1 and G2 phases. The S phase is usually significantly longer than the G1, G2 and mitotic phases.

However, the cells are not normally dividing synchronously and at the time of administration of a particular drug a random proportion of both normal and abnormal cells will be in a phase susceptible to attack. This means that the drug may be indiscriminate in its effects and if the treatment is at a dose level significantly effective against abnormal cells, a larger number of body cells may also be irreversibly damaged.

The present invention is based, in part, on the concept of using a drug to arrest the cell-division cycle reversibly in a particular phase, namely the metaphase, so that during the period when an effective amount of the drug remains in the system, a large number of both normal and abnormal cells reach that phase and stop dividing. When the drug has been eliminated from the system, cell division is resumed by affected cells and is initially synchronous. However, the normal and abnormal cells usually divide at markedly different rates and, considering the cells affected by the drug, after a few hours the abnormal cells will be synchronously in one phase while the normal cells will be in another. It is then possible to administer a drug which is effective against cells in the phase reached by the abnormal cells but not effective against cells in the phase reached by the normal cells. Thus, for example, hydroxyurea and cytosine arabinoside are effective against cells in the S-phase, while vincristine and vinblastine are effective against cells in the mitotic phase.

We have found that the compounds of the invention as defined hereinafter are useful in combating abnormal cell proliferation. In particular they have excellent metaphase arresting ability.

According to one aspect of the present invention, therefore, we provide compounds of general formula

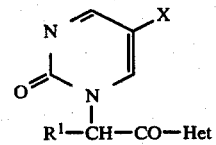

wherein
X represents a halogen atom or a trifluoromethyl group;
R¹ represents a hydrogen atom, or a lower alkyl group;
Het represents a C-attached 5–7 membered aromatic heterocyclic ring which ring contains one or more hetero atoms selected from O, N and S and optionally carries a fused ring and/or is optionally substituted by one or more substituents selected from halogen atoms and hydroxy, substituted hydroxy, amino, substituted amino, and $C_{1-4}$ alkyl groups; and, where a basic grouping is present, the salts thereof.

THe term "halogen" includes fluorine, chlorine, bromine and iodine.

The term "alkyl" or "lower alkyl" as used herein in relation to a group or part of a group (i.e. moiety), unless otherwise stated, preferably relates to such groups or moieties containing from 1 to 6, especially 1 to 4 carbon atoms. The term "aryl" as used herein in relation to a group or part of a group (i.e. moiety) preferably relates to a phenyl group. Preferred aralkyl groups contain from 7 to 10 carbon atoms. The term "substituted hydroxyl" as used herein includes alkoxy and aralkoxy, the alkyl and aralkyl moieties of which may be as defined above. The term "substituted hydroxyl" preferably relates to a $C_{1-4}$ alkoxy group. The term "substituted amino" as used herein includes amino groups carrying either one or two alkyl, aralkyl, aryl or alkanoyl, aralkanoyl or aroyl groups, as well as cyclic imido groups derived from dibasic alkanoic, aralkanoic or aroic acids.

X preferably represents a halogen atom, more preferably a chlorine or bromine atom.

Het represents a heterocyclic ring which preferably has 5 members. Het may, for example, contain one or two heteroatoms preferably one heteroatom. The heterocyclic ring may have another ring fused to it which ring may be carbocyclic e.g. a benzene or tetrahydrobenzene ring. Thus Het preferably represents a thienyl, furyl, thiazolyl or pyrrolyl group optionally carrying a fused benzene ring, the heterocyclic ring optionally being substituted by one or more halogen atoms e.g. bromine or $C_{1-4}$ alkyl groups e.g. methyl. Compounds of the invention are especially preferred in which Het represents a thienyl, methylthienyl, furyl, benzofuryl, dibromo-N-methylpyrrolyl or indolyl group.

R¹ is preferably methyl or more particularly, hydrogen.

Especially preferred compounds of formula I include the following:
(1) 5-bromo-1-(2-thenoylmethyl)pyrimidin-2-one,
(2) 5-chloro-1-(3-furoylmethyl)pyrimidin-2-one,
(3) 1-(3-furoylmethyl)-5-iodo-pyrimidin-2-one,
(4) 5-chloro-1-(benzo[b]furan-2-ylcarbonylmethyl)-pyrimidin-2-one,
(5) 5-chloro-1-(3-thenoylmethyl)pyrimidin-2-one,
(6) 5-chloro-1-[1-(2-thenoyl)ethyl]pyrimidin-2-one,
(7) 1-(4,5-dibromo-1-methylpyrrol-2-ylcarbonylmethyl)-5-chloropyrimidin-2-one.

(8) 5-chloro-1-(indol-3-ylcarbonylmethyl)pyrimidin-2-one,
(9) 5-chloro-1-(5-methyl-2-thenoylmethyl)pyrimidin-2-one,
(10) 5-chloro-1-(2-thenoylmethyl)pyrimidin-2-one,
(11) 5-bromo-1-(3-thenoylmethyl)pyrimidin-2-one,
of which compounds 9, 10 and 11 are particularly preferred.

Compounds according to the invention carrying hydroxy or amino groups may also in general, possess enhanced water-solubility, the latter, of course, forming acid addition salts for example with mineral acids such as e.g. hydrochloric or sulphuric acid or organic acids such as e.g. acetic, tartaric or citric acid.

It will be appreciated that the compounds according to the invention, depending on the groups present, may exist in a number of optical forms and all such forms as well as mixtures thereof are included within the scope of the invention.

It will be further appreciated that, for phramaceutical use, the salts referred to above will be physiologically compatible but other salts may find use, for example in the preparation of compounds of general formula I and their physiologically compatible salts.

The compounds of the invention are structurally quite simple and may be prepared by a variety of different processes. Reactions for the preparation of the six-membered pyrimidine ring system from ureas and three carbon atom components are well known in the art.

According to another aspect of the invention, therefore, we provide a process for the preparation of a compound of formula I as defined above wherein:

(a) A compound of the formula,

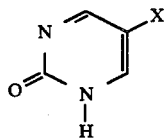
II (wherein X is as hereinbefore defined) or a salt thereof is reacted with an agent or agents serving to introduce the group

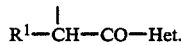

This agent may, for example, be a compound of formula:

$$R^1-CHY-CO-Het \qquad III$$

(wherein $R^1$ and Het are as hereinbefore defined and Y represents a leaving atom or group e.g. a halogen atom, a hydroxy group or a reactive ether or ester derivative).

A compound of formula III is advantageously used in which Y represents an iodine, bromine or chlorine atom or a hydrocarbonsulphonyloxy derivative such as a mesylate, brosylate or tosylate.

The reaction between the compounds of formula II and III is conveniently effected in the presence of a polar solvent such as an alkanol e.g. ethanol or dimethylformamide or a halogenated hydrocarbon such as dichloromethane. The reaction may also conveniently be effected in the presence of a base, e.g. a tertiary organic base such as triethylamine or an inorganic base e.g. an alkali metal hydroxide, such as potassium hydroxide, or an alkali metal carbonate, such as sodium carbonate, in the presence of a phase transfer catalyst such as benzyltrimethylammonium chloride. Where a salt of the compound of formula (II) is used, an added base will not normally be required. Such a salt may, for example, be an alkali metal, e.g. sodium or potassium, salt.

The group of formula

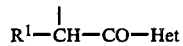

may also be introduced by a two stage reaction in which the compound of formula (II) is reacted with an O-silylating agent to form an O-silyl derivative e.g. a trialkylsilyl ether, followed by reaction with a compound of formula (III), preferably in the presence of a Lewis acid.

The reagent serving to introduce the group

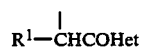

may, as indicated above, also be an alcohol of the formula $R^1CHOHCOHet$. In this case the reaction is carried out in the presence of a condensing agent such as an acetal of a $C_{1-5}$ dialkylformamide e.g. dimethyl formamide. The alkyl groups of the acetal are preferably neopentyl groups, thus dimethylformamide dineopentylacetal is a preferred condensing agent.

Alternatively, the compound of formula III may be in the form of an acetal of a $C_{1-5}$ dialkylformamide carrying at least one acetal group derived from the alcohol $R^1CHOHCOHet$.

(b) Deprotection of the protected keto group of a compound of the formula:

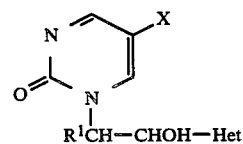
VII (wherein $R^1$, Het and X are as hereinbefore defined and $A^1$ represents a protected keto group). Deprotection may be effected according to conventional methods, for example by hydrolysis, e.g. basic hydrolysis using bases such as alkali metal hydroxides e.g. sodium or potassium hydroxide.

A compound of formula VII is preferably used in which the protected carbonyl group $A^1$ is in the form of a ketal group for example a ketal group derived from an alkanol, e.g. with 1 to 6 carbon atoms, such as methanol or ethanol or a 1,2-diol.

The compound of formula VII may be prepared by process (a) above or process (e) below.

(c) Oxidation of a compound of the formula:

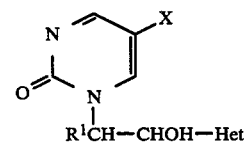
VIII (wherein R¹, Het and X are as hereinbefore defined).

The oxidation reaction may be effected using a reagent capable of oxidising a secondary hydroxyl group to a keto group, e.g. chromium trioxide/pyridine.

The compound of formula VIII may be prepared by any convenient method, for example by process (a) above, or process (e) below followed where required by deprotection of a protected hydroxymethylene group.

(d) A compound of formula I in which X is hydrogen may be converted into a compound in which X is halogen by electrophilic halogenation e.g. using molecular chlorine or bromine.

(e) A compound of formula:

$$\underset{O\phantom{XX}X\phantom{XX}O}{H-C-CH-CH} \qquad IV$$

(wherein X is as hereinbefore defined) or a functional derivative thereof such as an enol, acetal, enol ether, enol thioether, imine or enamine derivative, is reacted with a reagent serving to replace the oxo groups or functionally equivalent groups in formula IV by a urea moiety $$\underset{R^1-CHA\ Het}{-NH-CO-N-}$$

(wherein R¹, and Het are as hereinbefore defined and A represents a protected carbonyl, hydroxymethylene or protected hydroxymethylene group).

The group A in the reagent serving to replace the oxo groups by a urea moeity preferably represents a protected carbonyl group or a hydroxymethylene or protected hydroxymethylene group, in which case the compound formed by reaction of the compound of formula IV with the said reagent is further reacted, either to remove the carbonyl protecting group or to oxidise the —CHOH— group, (if necessary after removing the hydroxyl protecting group) whereby a compound of formula I is formed. The removal of the carbonyl or hydroxyl protecting groups or the oxidation of the hydroxymethylene group may, for example, be effected as described under process (b) and (c) hereinbefore.

In one variation, the compound of formula IV is reacted with a urea derivative of the formula, $$\underset{O}{NH_2-\underset{\|}{C}-NH-CHR^1-A-Het} \qquad V$$

(wherein A, R¹ and Het are as hereinbefore defined).

The reaction of the compounds of formula IV and V may conveniently be effected under acid conditions, preferably in a solvent such as, for example, an alcohol, e.g. ethanol. The reaction conveniently proceeds at room temperature.

The urea reagent of formula V may, if desired, be replaced by a cyanamide of formula $$Het-A-CHR^1-NH-C\equiv N$$

(wherein A, R¹ and Het are as hereinbefore defined) which reacts to form an intermediate of formula $$\underset{R^1-CH-A-Het}{\underset{|}{\underset{N}{X\diagdown\diagup\diagdown O}}\phantom{xx}\underset{C}{\overset{N}{\|\|}}} \qquad VI$$

(wherein A, R¹, Het and X are as hereinbefore defined) which may readily be cyclised, for example, in the presence of water.

Certain compounds of formula I may exist in salt form. Compounds of formula I carrying amino groups may form acid addition salts e.g. with mineral acids such as hydrochloric acid or sulphuric acid or organic acids such as acetic, tartaric or citric acid. Salts of the compounds of formula I may be converted to compounds of formula I per se by conventional techniques e.g. ion exchange.

According to a yet further feature of the present invention there are provided pharmaceutical compositions comprising as active ingredient, at least one compound of formula I as hereinbefore defined or, where a basic grouping is present, a physiologically compatible salt thereof in association with a pharmaceutical carrier or excipient.

For pharmaceutical administration the compounds of general formula I and their physiologically compatible salts may be incorporated into the conventional preparations in either solid or liquid form.

The compositions may, for example, be presented in a form suitable for rectal, parenteral or topical administration. Preferred forms include, for example suspensions, suppositories, creams, ointments and lotions and solutions e.g. for injection or infusion or for ingestion by the gastro-intestinal tract. Solutions for injection are especially preferred.

The active ingredient may be incorporated in excipients customarily employed in pharmaceutical compositions such as, for example cocoa butter, aqueous or non-aqueous vehicles, fatty substances of animal or vegetable origin, paraffin derivatives, glycols, various wetting, dispersing or emulsifying agents and/or preservatives.

Advantageously the compositions may be formulated as dosage units, each unit being adapted to supply a fixed dose of active ingredient. Suitable dosage units for adults contain from 50 mg to 1.0 g of active ingredient.

According to a further feature of the present invention there is provided a method of combating, or a method for the prophylaxis of abnormal cell proliferation in a host which comprises administering to said host an effective amount of a compound of formula I or, where a basic grouping is present, a physiologically compatible salt thereof. The dosage, which may be varied according to the compound used, the subject treated and the complaint concerned, may, for example, be from 0.25 to 7.0 g in a day in adults.

It will normally be necessary to have a knowledge of cell cycle kinetics (for example as determined by cytofluorometry) of both the normal and abnormal cells and to prepare time schedules which indicate how long after administration of the drug the majority of the abnormal cells will reach a phase which is susceptible to attack by a chosen cytotoxic drug while the majority of normal cells are in a non-susceptible phase. These periods will naturally differ widely. Suitable cytotoxic drugs include cytosine arabinoside and hydroxyurea which are cytotoxic against cells in the S-phase. Since the S-phase is generally longer than the other phases, it is easier to find appropriate time schedules when using cytotoxic drugs active in this phase.

The following Examples are given by way of illustration only.

Melting points were determined on a Kofler block and are uncorrected. Analytical t.l.c. was carried out on ready-made Merck Kieselgel 60 $F_{254}$ plates (silica) and products were detected by their fluorescence quenching at 254 n.m. and by their staining with iodine vapour. P.l.c. was performed on Merck Kieselgel 60 $PF_{254+366}$. Products were detected at 254 n.m.

EXAMPLE 1

5-Chloro-1-(2-thenoylmethyl)pyrimidin-2-one

Method A

A mixture of 5-chloropyrimidin-2-one hydrochloride (0.668 g) and 2-bromoacetylthiophene (0.820 g) in ethanol (25 ml) was treated at room temperature with triethylamine (1.3 ml). After stirring at room temperature for 6 days the reaction mixture was cooled in an ice-bath and the precipitate was collected, washed with cold ethanol and dried to give an off white crystalline solid (0.536 g). The solid was crystallised once from acetone and then once from ethanol to give colourless needles of the title pyrimidinone (0.207 g). m.p. 209°–211° C. (Kofler). $\lambda_{max}$ (EtOH) 226 nm ($\epsilon$ 9,530), 260 nm ($\epsilon$ 8,430), 288 nm ($\epsilon$ 6,830).

Method B

A mixture of 5-chloropyrimidin-2-one (50 mg) anhydrous sodium carbonate (106 mg) 2-bromoacetylthiophene (92 mg) and benzyltrimethylammonium chloride (3 mg) in N,N-dimethylformamide (3 ml) was stirred at room temperature. After 1 hour the purple reaction mixture was diluted with water (30 ml) and extracted with ethyl acetate ($\times$3). The combined extracts were washed with water, dried (MgSO$_4$) and evaporated to a yellow gum (60 mg), identical with the sample from method A by thin layer chromatography (silica, chloroform-ethanol 19:1, $R_f$ 0.46).

EXAMPLE 2

5-Bromo-1-(2-thenoylmethyl)pyrimidin-2-one

A suspension of 5-bromopyrimidin-2-one hydrobromide (780 mg) and 2-bromoacetylthiophene (633 mg) in triethylamine (1 ml) and ethanol (20 ml) was stirred at ambient temperature for 1½ hours. A solution formed within 10 minutes but a suspension subsequently resulted. This was chilled in ice, and the collected solid was crystallised from acetone to give the title pyrimidinone: yield 293 mg; m.p. 173°–175° C. dec; $\lambda_{max}^{EtOH}$ 259.5 nm ($\epsilon$ 9470), 287 nm ($\epsilon$ 6830), 332 nm ($\epsilon$ 2780).

EXAMPLE 3

5-Chloro-1-(3-furoylmethyl)pyrimidin-2-one

A mixture of 5-chloropyrimidin-2-one (587 mg) and crude 3-bromoacetylfuran (2.00 g, ca. 4.5 mmol, based on purity ca. 40% by $^1$H n.m.r; contaminated with 3-dibromoacetylfuran and diethyl ether) in triethylamine (0.95 ml) and ethanol (25 ml) was stirred at room temperature. After 45 min with solvent was removed and the residue triturated with ethyl acetate. The resulting solid was collected and retriturated with water. This gave a buff solid which was crystallised from ethyl acetate to give the title pyrimidinone (335 mg), m.p. 195°–197° C. (dec), $\lambda_{max}$ (EtOH) 333 nm ($\epsilon$ 2,530).

EXAMPLE 4

1-(3-Furoylmethyl)-5-iodopyrimidin-2-one

A mixture of 5-iodopyrimidin-2-one (1.00 g) and crude 3-bromoacetylfuran (1.95 g, ca. 4.5 mmol, based on purity ca. 40% by $^1$H n.m.r; contaminated with 3-dibromoacetylfuran and diethyl ether) in triethylamine (0.95 ml) and ethanol (25 ml) was stirred at room temperature. After 1 h the solvent was evaporated and the residue was dissolved in ethyl acetate. The solution was washed with water ($\times$3), dried (MgSO$_4$) and evaporated to a gum. Preparative thin-layer chromatography of the gum on silica developing with chloroform-ethanol (24:1) (2 runs) gave a solid which was crystallised twice from ethyl acetate to give the title pyrimidinone as a solvent (0.1 mol EtOAc) (240 mg), m.p. 160°–162° C. (dec), $\lambda_{max}$ (EtOH) 228.5 nm ($\epsilon$ 17,400), 339 nm ($\epsilon$2,670).

EXAMPLE 5

5-Chloro-1-(benzo[b]furan-2-ylcarbonylmethyl)pyrimidin-2-one

A mixture of 5-chloropyrimidin-2-one (522 mg) and 2-bromoacetylbenzo[b]furan (960 mg) in triethylamine (0.84 ml) and ethanol (25 ml) was stirred at room temperature. After 50 min the reaction mixture was cooled to 3° C. and the solid collected. The filtrate was evaporated and the residue was subjected to preparative thin-layer chromatography developing with chloroform-ethanol (50:1) (4 runs) which gave a yellow solid. The two solids were combined and crystallised twice from acetone to give the title pyrimidinone (415 mg) m.p. 202°–205° C., $\lambda_{max}$ (EtOH) 227.5 nm ($\epsilon$14,060), 298 nm ($\epsilon$20,930).

EXAMPLE 6

5-Fluoro-1-(2-thenoylmethyl)pyrimidin-2-one

A mixture of 5-fluoropyrimidin-2-one (456 mg) and 2-bromoacetylthiophene (820 mg) in triethylamine (1.33 ml) and ethanol (25 ml) was stirred at room temperature. After 2.5 h. the reaction mixture was concentrated to ca. 5 ml, diluted with ethyl acetate (300 ml) washed with water (3$\times$50 ml), dried (MgSO$_4$) and evaporated to a foam. This was crystallised from acetone to give the title pyrimidinone (225 mg), m.p. 183°–190° C. (dec) $\lambda_{max}$ (EtOH) 260 nm ($\epsilon$10,308), 285.5 nm ($\epsilon$ 8,430).

EXAMPLE 7

5-Chloro-1-(3-thenoylmethyl)pyrimidin-2-one

A mixture of 5-chloropyrimidin-2-one (522 mg) and 3-bromoacetylthiophene (1.025 g) in triethylamine (0.84 ml) and ethanol (25 ml) was stirred at room temperature. After 1 h. the mixture was cooled to 3° C., the resulting precipitate was collected, then dried and recrystallised twice from ethanol to give the title pyrimidinone (460 mg), m.p. 227°–230° C., $\lambda_{max}$ (EtOH) 250 nm ($\epsilon$ 15,770), 333 nm ($\epsilon$ 2,690).

EXAMPLE 8

5-Chloro-1-(5-methyl-2-thenoylmethyl)pyrimidin-2-one

A mixture of 5-chloropyrimidin-2-one (522 mg) and 2-bromoacetyl-5-methylthiophene (1.30) g) in triethylamine (0.84 ml) and ethanol (25 ml) was stirred at room temperature. After 2 h. the mixture was concentrated to ca. 10 ml, diluted with ethyl acetate (100 ml), washed with water (×3) and brine, dried (MgSO$_4$) and evaporated to a gum. The gum was triturated with diethyl ether and the resulting solid dissolved in ethanol and treated with charcoal. Evaporation of the solvent followed by recrystallisation of the residue twice from ethyl acetate gave the title pyrimidinone (205 mg) m.p. 199°–203° C., $\epsilon_{max}$ (EtOH) 226.5 nm ($\epsilon$8,570), 261.5 nm ($\epsilon$9,280), 297 nm ($\epsilon$11,630).

EXAMPLE 9

5-Chloro-1-[1-(2-thenoyl)ethyl]pyrimidin-2-one

A mixture of 5-chloropyrimidin-2-one (522 mg) and 2-(2-bromopropionyl)thiophene (965 mg) in triethylamine (0.84 ml) and ethanol (25 ml) was stirred at room temperature. After 3 h. the mixture was heated to 50° C. After a further 1 h. the solvent was removed and the residue dissolved in ethyl acetate (50 ml) which was washed with water (3×25 ml) and brine, dried (MgSO$_4$) and evaporated to a yellow oil. The oil was triturated with diethyl ether and the resulting solid was crystallised twice from ethyl acetate to give the title pyrimidinone (320 mg), m.p. 128°–129° C., $\lambda_{max}$ (EtOH) 226 nm ($\epsilon$ 11,340), 263 nm ($\epsilon$10,050), 290 nm ($\epsilon$ 8,950).

EXAMPLE 10

5-Bromo-1-(3-thenoylmethyl)pyrimidin-2-one

A mixture of 5-bromopyrimidin-2-one (700 mg) and 3-bromoacetylthiophene (1.025 g) in triethylamine (0.84 ml) and ethanol (25 ml) was stirred at room temperature. After 1 h. the mixture was cooled to 3° C. and the precipitate collected. The dried solid was crystallised from ethanol to give the title pyrimidinone (475 mg), m.p. 180°–182° C. (dec), $\lambda_{max}$ (EtOH) 250.5 nm ($\epsilon$ 14,930), 334.5 nm ($\epsilon$ 3,260).

EXAMPLE 11

1-(4,5-Dibromo-1-methylpyrrol-2-ylcarbonylmethyl)-5-chloropyrimidin-2-one

A mixture of 5-chloropyrimidin-2-one (522 mg) and 2,3-dibromo-5-bromoacetyl-1-methylpyrrole (1.24 g) in triethylamine (0.84 ml) and ethanol (35 ml) was stirred at room temperature. After 1.25 h the reaction mixture was cooled in ice and the white precipitate collected and washed with cold ethanol. The dried solid was crystallised twice from ethanol and then from ethyl acetate to give the title pyrimidinone (510 mg) m.p. 229°–232° C., $\lambda_{max}$ (EtOH) 227 nm ($\epsilon$9,750), 249 nm ($\epsilon$9.540), 301.5 nm ($\epsilon$16,910).

EXAMPLE 12

5-Chloro-1-(indol-3-ylcarbonylmethyl)pyrimidin-2-one

A mixture of 5-chloropyrimidin-2-one (522 mg) and 3-bromoacetylindole (1.19 g) in triethylamine (0.84 ml) and ethanol (25 ml) was stirred at room temperature. After 1.5 h the mixture was heated to 55° C. After a further 1.5 h the mixture was cooled and the resulting precipitate collected and washed with cold ethanol. Recrystallisation twice from ethyl acetate and once from ethanol gave the title pyrimidinone (660 mg), m.p. 228°–229° C., $\lambda_{max}$ (EtOH) 240 nm ($\epsilon$ 16,370) 300.5 nm ($\epsilon$ 13,090).

EXAMPLE 13

5-Chloro-1-(4-methylthiazol-5-ylcarbonylmethyl)-pyrimidin-2-one

A suspension of 5-chloropyrimidin-2-one (392 mg) and 5-bromoacetyl-4-methylthiazole (660 mg) in dry dichloromethane was treated with triethylamine (0.42 ml) and the resulting pale yellow solution was stirred at room temperature. After 1.25 h a precipitate had formed and the mixture was cooled in an ice-bath. The solid was collected, washed with cold dichloromethane and dried (346 mg). A second crop was obtained by concentration of the mother liquors (255 mg). The combined solids were recrystallised from acetone and then dichloromethane to give white crystals, the title pyrimidinone (186 mg) m.p. 212°–215° C. $\lambda_{max}$ (EtOH) 250.5 nm (E$_{1cm}^{1\%}$ 403), 266.5 nm (E$_{1cm}^{1\%}$ 401), 334 nm (E$_{1cm}^{1\%}$ 65). High performance liquid chromatography (reverse phase column, acetonitrilewater, 1:3) showed only one major component. N.M.R. (DMSO d$^6$): 0.68 (2'-H), 1.28, 1.54 (two doublets, J 4 Hz) (4,6-H), 4.69 (—CH$_2$—), 7.21 $\tau$ (4'-CH$_3$).

EXAMPLE 14

5-Chloro-1-(4,5,6,7-tetrahydrobenzo[b]thien-2-ylcarbonylmethyl)pyrimidin-2-one

A mixture of 5-chloropyrimidin-2-one (370 mg) and 2-bromoacetyl-4,5,6,7-tetrahydrobenzo[b]thiophene (740 mg) in ethanol (15 ml) was treated with triethylamine (0.6 ml, 4.76 mmol) and then stirred at room temperature. After 1.5 h the mixture was concentrated to ca 5 ml and then diluted with ethyl acetate (50 ml). The resulting solution was washed with water (×3), dried (MgSO$_4$) and evaporated to a pale yellow foam. The foam was subjected to preparative thin-layer chromatography on silica developing with chloroform-ethanol (29:1) (two runs). Elution of the major band with ethyl acetate gave a white solid which was crystallised from ethyl acetate to give the title pyrimidinone (290 mg), m.p. 206°–208° C., $\lambda_{max}$ (EtOH) 225 nm ($\epsilon$ 10,160), 268.5 nm ($\epsilon$ 9,570), 314 nm ($\epsilon$ 12,260).

PREPARATION 1

2,3-Dibromo-5-bromoacetyl-1-methylpyrrole

A stirred solution of 2-acetyl-1-methylpyrrole (2.00 g) in diethyl ether (13 ml) and dioxan (26 ml) was cooled to below 10° C. and then treated with bromine (1.85 ml) over 30 min maintaining the temperature below 10° C. When the addition was complete the mixture was allowed to warm to room temperature for 30 min and then heated to 55° C. After a further 1.5 h the solution was cooled and concentrated. The residue was diluted with chloroform (100 ml) and washed with water (×3), dried (MgSO$_4$) and evaporated to an oil. The oil was subjected to column chromatography on silica developing the eluting with chloroform-petrol (b.p. 60°–80° C.) (1:1). This gave the title pyrrole (1.90 g), m.p. 89°–94° C., $\lambda_{max}$ (EtOH) 311 nm ($\epsilon$ 14,105).

PREPARATION 2

2-(2-Bromopropionyl)thiophene

An ice cold solution of 2-propionylthiophene (1.40 g) in carbon tetrachloride (25 ml) was treated with a solution of bromine (0.54 ml) in carbon tetrachloride (20 ml) over 5 mins. The resulting solution was then stirred at room temperature. After 1.5 h the mixture was evaporated to an amber oil (2.17 g). A portion of the oil (600 mg) was subjected to preparative thin-layer chromatography on silica developing with chloroform-petrol (b.p. 60°–80° C.) (1:4) (4 runs) and gave an amber oil, the title bromide (410 mg), $\lambda_{max}$ (EtOH) 272.5 nm ($\epsilon$7,910), 294 nm ($\epsilon$8,340), $\nu_{max}$ (CS$_2$) 1658, 713 cm$^{-1}$.

PHARMACEUTICAL COMPOSITION EXAMPLES

EXAMPLE A

Injection solution

1. Active ingredient: 50 mg
2. Polysorbate 80: 2.50 mg
3. Sodium chloride: 45 mg
4. Water for injection: to 5.0 ml The sterile active ingredient, precipitated as a very fine powder, is dispersed aseptically in an aqueous vehicle containing the wetting agent (Polysorbate 80) and sufficient sodium chloride to produce an approximately isotonic solution thus providing a suspension which may be used for deep intrasmuscular injection. Buffer salts may be incorporated (with a consequent reduction in the quantity of sodium chloride) to provide a suspension at the appropriate pH to ensure optimum stability of the compound before injection. The product may be presented as a dry filled vial of active ingredient together with a sterile ampoule of the remaining ingredients to permit extemporaneous preparation of the suspension immediately before injection.

EXAMPLE B

Injection solution

1. Active ingredient: 100 mg
2. Aluminium monostearate: 5 mg
3. Fractionated coconut oil to 1 ml Sterile active ingredient in the form of a very fine powder is dispersed aseptically in a sterile oily vehicle containing a suspending agent whose structure is built up during the heat sterilisation of the vehicle. Such a product may be presented as a pre-prepared suspension for intrasmuscular injection. The dose administered may be adjusted by alteration of the dose volume. The product may be presented in multidose vials, sealed with oil resistant rubber plugs to permit withdrawal of the required dose volume.

We claim:

1. Compounds of the formula:

[structure: pyrimidin-2-one with substituent X at 5-position and R$^1$—CH—CO—Het at N-1]

wherein

X represents a halogen atom or a trifluoromethyl group;
R$^1$ represents a hydrogen atom or a lower alkyl group;
Het represents a C-attached 5 membered aromatic heterocyclic ring having one or two hetero atoms selected from O, N and S and optionally carries a fused benzene or tetrahydrobenzene ring and is optionally substituted by up to three substituents selected from halogen atoms, hydroxy, alkoxy in which the alkyl moiety has from 1 to 6 carbon atoms, aralkoxy in which the aralkyl moiety has from 7 to 10 carbon atoms, amino, amino substituted with one or two groups selected from alkyl groups having from 1 to 6 carbon atoms, aralkyl having from 7 to 10 carbon atoms, phenyl, alkanoyl in which the alkyl moiety has from 1 to 6 carbon atoms and phenylalkanoyl in which the alkyl moiety has from 1 to 6 carbon atoms, and alkyl having from 1 to 4 carbon atoms; and, where a basic group is present, the pharmaceutically acceptable salts thereof.

2. Compounds as claimed in claim 1 wherein Het represents a thienyl, furyl, thiazolyl or pyrrolyl group optionally carrying a fused benzene ring, the heterocyclic ring optionally being substituted by one to three halogen atoms or C$_{1-4}$ alkyl groups.

3. Compounds as claimed in claim 2 wherein Het represents a thienyl, methylthienyl, furyl, benzofuryl, dibromo-N-methylpyrrolyl or indolyl group.

4. Compounds as claimed in claim 1 wherein R$^1$ represents a hydrogen atom.

5. Compounds as claimed in claim 1 wherein X represents a halogen atom.

6. Compounds as claimed in claim 1 which are:
5-bromo-1-(2-thenoylmethyl)pyrimidin-2-one,
5-chloro-1-(3-furoylmethyl)pyrimidin-2-one,
1-(3-furoylmethyl)-5-iodopyrimidin-2-one,
5-chloro-1-(benzo[b]furan-2-ylcarbonylmethyl)pyrimidin-2-one,
5-chloro-1-(3-thenoylmethyl)pyrimidin-2-one,
5-chloro-1-[1-(2-thenoyl)ethyl]pyrimidin-2-one,
1-(4,5-dibromo-1-methylpyrrol-2-ylcarbonylmethyl)-5-chloropyrimidin-2-one.
5-chloro-1-(indol-3-ylcarbonylmethyl)pyrimidin-2-one.

7. A compound as claimed in claim 1 which is 5-chloro-1-(5-methyl-2-thenoylmethyl)pyrimidin-2-one.

8. A compound as claimed in claim 1 which is 5-chloro-1-(2-thenoylmethyl)pyrimidin-2-one.

9. A compound as claimed in claim 1 which is 5-bromo-1-(3-thenoylmethyl)pyrimidin-2-one.

10. Pharmaceutical compositions comprising as active ingredient at least one compound of formula I as defined in claim 1 or, where a basic group is present, a physiologically compatible salt thereof in association with a pharmaceutical carrier or excipient.

11. A method of arresting abnormal cell proliferation in a host which comprises administering to said host an effective amount of a compound of formula I as defined in claim 1 or, where a basic group is present, a physiologically compatible salt thereof.

* * * * *